United States Patent [19]
Yamada et al.

[11] Patent Number: 5,965,059
[45] Date of Patent: Oct. 12, 1999

[54] OPTICALLY ACTIVE COMPOUND, ANTIFERROELECTRIC LIQUID CRYSTAL COMPOSITION CONTAINING THE SAME, PROCESS FOR PRODUCING THE SAME AND PROCESS FOR PRODUCING AN OPTICALLY ACTIVE CARBOXYLIC ACID

[75] Inventors: Shinya Yamada; Yukiharu Iwaya; Mamoru Yamada; Akio Yamaguchi; Hitoshi Kondo; Toshimitsu Hagiwara, all of Kanagawa, Japan

[73] Assignee: Takasago International Corporation, Tokyo, Japan

[21] Appl. No.: 09/044,123

[22] Filed: Mar. 19, 1998

[30] Foreign Application Priority Data

Jun. 13, 1997 [JP] Japan ..................................... 9-171246
Nov. 19, 1997 [JP] Japan ..................................... 9-333712

[51] Int. Cl.⁶ ........................... C09K 19/34; C07C 22/00; C07C 69/73; C07D 239/02
[52] U.S. Cl. .................... 252/299.61; 544/298; 560/227; 570/144; 570/136
[58] Field of Search ....................... 544/298; 252/299.61; 570/144, 136; 560/227

[56] References Cited

U.S. PATENT DOCUMENTS

| | | | |
|---|---|---|---|
| 4,900,472 | 2/1990 | Miyazawa et al. ................. | 252/299.61 |
| 4,918,213 | 4/1990 | Nohira et al. ............................ | 558/271 |
| 5,073,306 | 12/1991 | Nohira et al. ........................ | 252/299.61 |
| 5,110,496 | 5/1992 | Mogamiya et al. ............... | 252/299.61 |
| 5,126,482 | 6/1992 | Nakai et al. ............................. | 554/150 |
| 5,128,472 | 7/1992 | Osawa et al. ........................... | 544/335 |
| 5,211,879 | 5/1993 | Shiratori et al. .................... | 252/299.67 |
| 5,391,318 | 2/1995 | Yamashita et al. ................ | 252/299.61 |
| 5,427,714 | 6/1995 | Murashiro et al. ................. | 252/299.61 |
| 5,545,345 | 8/1996 | Sekine et al. ....................... | 252/299.61 |
| 5,585,036 | 12/1996 | Wand et al. ......................... | 252/299.01 |
| 5,665,270 | 9/1997 | Fukushima et al. ............... | 252/299.01 |
| 5,716,542 | 2/1998 | Iwaya et al. ........................ | 252/299.61 |
| 5,779,934 | 7/1998 | Higashi et al. ..................... | 252/299.61 |
| 5,820,872 | 10/1998 | Yamada et al. ..................... | 252/299.61 |

FOREIGN PATENT DOCUMENTS 350334  1/1990  European Pat. Off. .
0 474 196  3/1992  European Pat. Off. .

*Primary Examiner*—C. H. Kelly
*Attorney, Agent, or Firm*—Sughrue, Mion, Zinn, Macpeak & Seas, PLLC

[57] ABSTRACT

An optically active compound which itself generally exhibits no antiferroelectric liquid crystal phase, but which can be added to an antiferroelectric liquid crystal or composition thereof having a high threshold voltage to reduce the threshold voltage of the resulting composition. Also disclosed is an antiferroelectric liquid crystal composition containing the optically active compound, a process for reducing the threshold voltage of an antiferroelectric liquid crystal composition, a process for producing the optically active compound, and a process for producing an optically active carboxylic acid as an intermediate.

5 Claims, 1 Drawing Sheet

OPTICALLY ACTIVE COMPOUND, ANTIFERROELECTRIC LIQUID CRYSTAL COMPOSITION CONTAINING THE SAME, PROCESS FOR PRODUCING THE SAME AND PROCESS FOR PRODUCING AN OPTICALLY ACTIVE CARBOXYLIC ACID

FIELD OF THE INVENTION

The present invention relates to a novel optically active compound useful as a component of a liquid crystal material for an optical switching element. More particularly, the present invention relates to an antiferroelectric liquid crystal composition containing the optically active compound. In addition, the present invention relates to a process for producing the optically active compound, and also relates to a process for producing an optically active carboxylic acid which is used for preparing the optically active compound.

BACKGROUND OF THE INVENTION

The antiferroelectric liquid crystal was discovered by Chandani et al. in 1988 (Chandani et al., *Jpn.J.Appl.Phys.*, 27, L279 (1988)), and has been proposed as a future material substituting for nematic liquid crystals which are presently used in liquid crystal displays.

The switching time of the nematic liquid crystal which is presently used in liquid crystal displays is typically as slow as 30 milliseconds. Thus, these display devices are fabricated using a driving method employing a thin film transistor (TFT) called an active matrix having a very high production cost. Furthermore, a display based on a twisted nematic (TN) system is disadvantageous in that it essentially provides a narrow viewing angle.

The antiferroelectric liquid crystal has a switching time as fast as several tens of microseconds. In the antiferroelectric liquid crystal, liquid crystal molecules respond in plane such that a wide viewing angle can be obtained. Furthermore, the antiferroelectric liquid crystal exhibits a definite threshold voltage even under an applied DC voltage and is thus easily driven. Accordingly, the antiferroelectric liquid crystal can constitute a display device driven by a simple matrix requiring a low production cost.

On the other hand, a ferroelectric liquid crystal disclosed by Meyer et al. in 1975 (R. B. Meyer et al., *J. Phys.* (France), 36, L69, (1975)) was proposed as a high definition liquid crystal display because of its fast response. However, a full color image display using the ferroelectric liquid crystal has not yet been realized because of the difficulty in producing gray levels. With the antiferroelectric liquid crystal, a gray scale has been realized. Therefore, a full-color animation display has already been achieved, though on an experimental basis.

As mentioned above, the liquid crystal display employing an antiferroelectric liquid crystal is expected to achieve a high definition display having a wide viewing angle using a low cost simple matrix.

However, compounds exhibiting an antiferroelectric liquid crystal phase are extremely restricted from a structural viewpoint. Most of these compounds have a terminal structure such as a 1-substituted alkyl benzoic acid ester exemplified by the following structural formula (see *Future Liquid Crystal Display and Its Materials*, supervised by Atsuo Fukuda, CMC, (1992)):

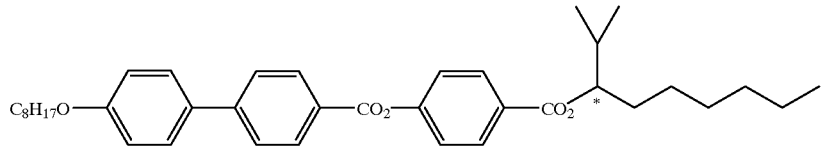

wherein Y represents an alkyl group or a perfluoroalkyl group.

The antiferroelectric liquid crystal incorporated into display devices must have a practical working temperature range such as nematic liquid crystals in general use and must also exhibit various properties relating to display quality. Thus, it is necessary to mix antiferroelectric liquid crystal compounds having different properties to form the desired liquid crystal composition. However, because the structure that allows the appearance of an antiferroelectric liquid crystal phase is restricted as mentioned above, the only allowable structural modifications are the introduction of an alicyclic group, condensed ring or heterocyclic group into the core structure and the introduction of an ether bond into the chiral terminal alkyl chain. The resulting compound is much like the original compound in its properties. Thus, a practical liquid crystal composition having the above properties is difficult to obtain.

Thus, the development of liquid crystal compounds having a range of properties is indispensable in obtaining an antiferroelectric liquid crystal having practically useful properties.

On the other hand, the present inventors have found that a compound having the following structure can exhibit an antiferroelectric liquid crystal phase (see JP-A-4-82862 (The term "JP-A" as used herein means an "unexamined published Japanese patent application")).

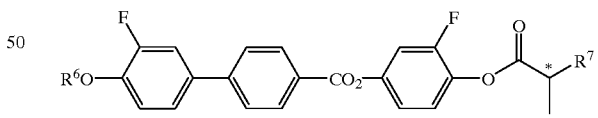

This compound has 2-methylalkanoic acid incorporated therein and thus exhibits a stable antiferroelectric liquid crystal phase. However, this compound has a high viscosity because its core structure is similar to that of known antiferroelectric liquid crystals and also has a high threshold voltage. The present inventors also found that an antiferroelectric liquid crystal phase appears when 2-methylalkanoic acid is introduced into the core of a heterocyclic compound such as diphenylpyrimidine (see JP-A-9-31063). This compound has a lower viscosity than the foregoing ester compounds and thus is useful. However, this compound also has a high threshold voltage. That is, there is a need to solve the above problems of the prior art.

SUMMARY OF THE INVENTION

It is therefore an object of the present invention to provide a novel optically active compound which itself generally exhibits no antiferroelectric liquid crystal phase but which can be incorporated into an antiferroelectric liquid crystal composition having a high threshold voltage to lower the threshold voltage of the resulting composition, an antiferroelectric liquid crystal composition containing the novel optically active compound, and a process for producing the novel optically active compound and its intermediate at a low cost.

The present inventors sought an optically active compound which can reduce the threshold voltage of the foregoing antiferroelectric liquid crystal compound having a high threshold voltage. As a result, the present inventors discovered an optically active compound which itself generally exhibits no antiferrelectric liquid crystal phase but which can be incorporated into the foregoing antiferroelectric liquid crystal or antiferroelctric liquid crystal-containing composition having a high threshold voltage to lower the threshold voltage of the resulting composition. Furthermore, the optically active compound and notably its intermediate can be produced by a low cost process. Thus, the present invention has been achieved based on the above findings.

Thus, a first aspect of the present invention relates to an optically active compound, and more particularly, to an optically active compound represented by the following general formula (1):

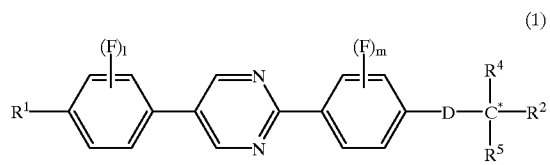

(1)

wherein $R^1$ represents an alkyl or alkoxy group having 5 to 14 carbon atoms; $R^2$ represents an alkyl group having 2 to 12 carbon atoms; l and m each represents 0 or 1; D represents —OCO—, —CH$_2$—O— or —OCOC*R$^3$H—, with the proviso that when D is —OCO—, $R^4$ represents a fluorine atom or a trifluoromethyl group and $R^4$ represents a hydrogen atom or a fluorine atom, when D is —CH$_2$—O—, $R^4$ represents a methyl group or a trifluoromethyl group and $R^5$ represents a hydrogen atom, when D is —OCOC*R$^3$H—, $R^3$ is a methyl group, $R^4$ is a fluorine atom or an alkyl group having 1 to 5 carbon atoms, $R^5$ is a hydrogen atom, and $R^2$ may form a ring with $R^3$; and C* represents an asymmetric carbon atom.

A second aspect of the present invention relates to a liquid crystal composition, and more particularly, to an antiferroelectric liquid crystal composition containing at least one optically active compound represented by the foregoing general formula (1).

A third aspect of the present invention relates to a process, and more particularly, to a process for reducing the threshold voltage of an antiferroelectric liquid crystal composition which comprises incorporating at least one optically active compound represented by the foregoing general formula (1) into an antiferroelectric liquid crystal or composition thereof.

A fourth aspect of the present invention relates to a process, and more particularly, to a process for producing an optically active compound represented by the foregoing general formula (1), which comprises reacting a compound represented by the following general formula (2):

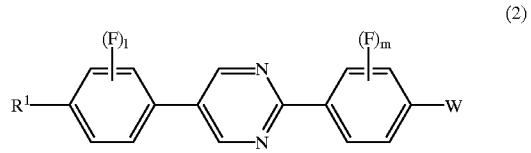

(2)

wherein $R^1$ represents an alkyl or alkoxy group having 5 to 14 carbon atoms; l and m each represents 0 or 1; and W represents a hydroxy group, chloromethyl group or bromomethyl group, with the following compound represented by general formula (3):

(3)

wherein $R^2$ represents an alkyl group having 2 to 12 carbon atoms; X represents COOH, COCl a hydroxymethyl group, —C*R$^3$HCOOH or —C*R$^3$HCOCl with the proviso that when X is COOH or COCl, $R^4$ represents a fluorine atom or a trifluoromethyl group and $R^5$ represents a hydrogen atom or a fluorine atom, when X is a hydroxymethyl group, $R^4$ represents a methyl group or a trifluoromethyl group and $R^5$ represents a hydrogen atom, when X is —C*R$^3$HCOOH or —C*R$^3$HCOCl, $R^3$ is a methyl group, $R^4$ is a fluorine atom or an alkyl group having 1 to 5 carbon atoms, $R^5$ is a hydrogen atom, and $R^2$ may form a ring with $R^3$; and C* represents an asymmetric carbon atom.

A fifth aspect of the present invention relates to a process, and more particularly, to a process for producing an optically active carboxylic acid represented by general formula (4):

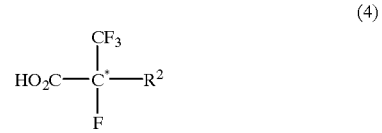

(4)

wherein $R^2$ represents an alkyl group having 4 to 12 carbon atoms; and C* represents an asymmetric carbon atom, which comprises reacting an optically active 1-alkylallylalcohol with hexafluoropropene diethylamine.

DETAILED DESCRIPTION OF THE INVENTION

Figure 1:
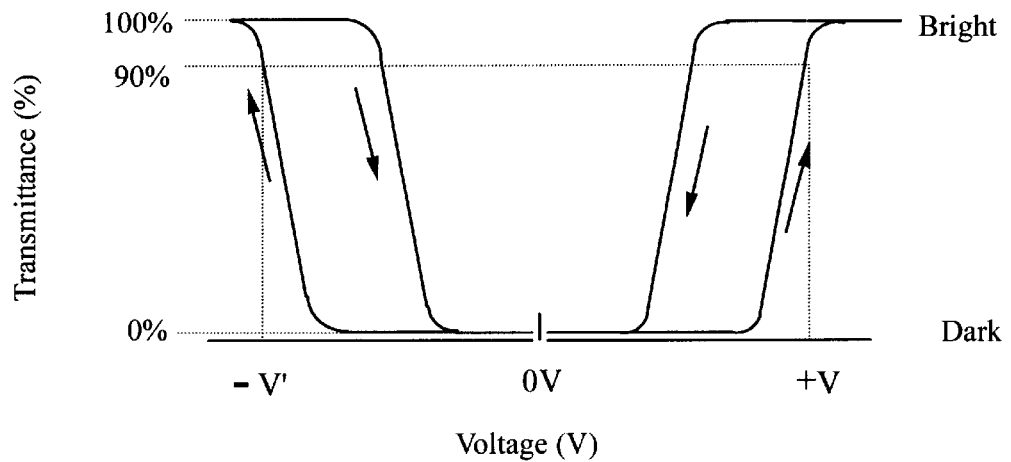
FIG. 1 illustrates the electro-optic response (double hysteresis) of an antiferroelectric liquid crystal, and further defines $V_{th}$ (threshold voltage) where $V_{th}=(V+V')/2$.
Figure 2:
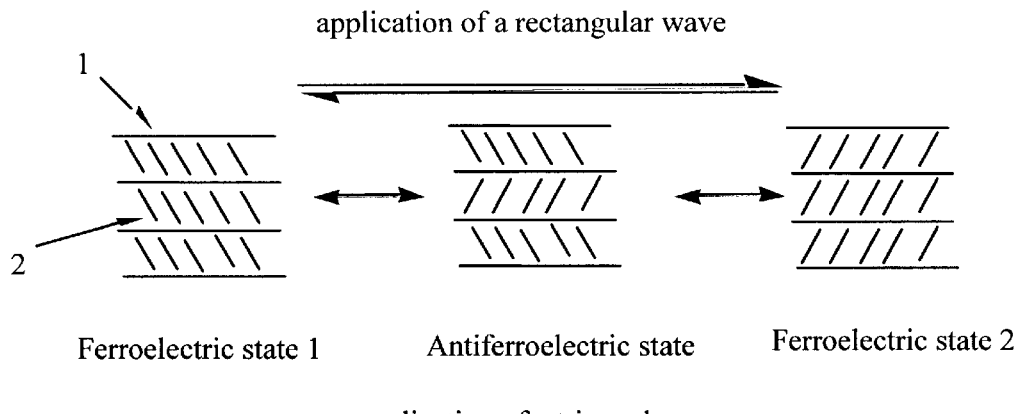
FIG. 2 is a diagram showing the typical response of an antiferroelectric liquid crystal 2 constituting layer 1 under an applied rectangular or triangular wave.

The present invention is described in further detail below.

Examples of the preferred optically active compound of the present invention represented by general formula (1) are given below.

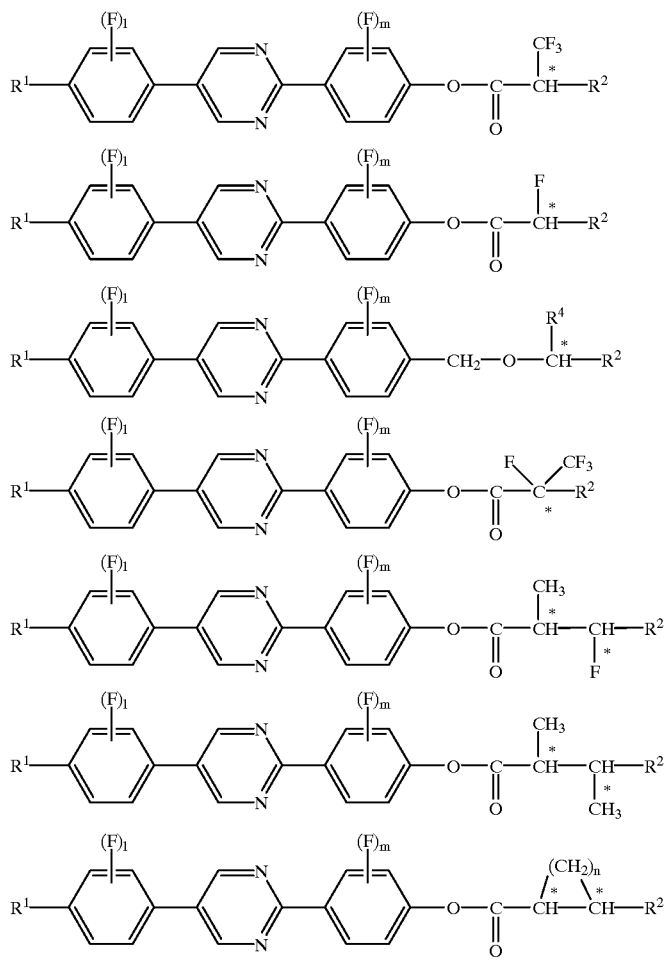

wherein $R^1$, $R^2$, $R^4$, l, and m have the same meanings as described above, n is an integer of from 2 to 4, $R^1$ is selected from the group consisting of a pentyl group, hexyl group, heptyl group, octyl group, nonyl group, decyl group, undecyl group, dodecyl group, tridecyl group and tetradecyl group or an alkyloxy group thereof, and $R^2$ is selected from the group consisting of an ethyl group, propyl group, butyl group, pentyl group, hexyl group, heptyl group, octyl group, nonyl group, decyl group, undecyl group and dodecyl group, $C_{1-11}$ methyl-substituted alkyl group, $C_{3-10}$ ethyl-substituted alkyl group, $C_{3-10}$ dimethyl-substituted alkyl group, $C_{4-9}$ propyl-substituted alkyl group and trimethylalkyl group.

Most of the compounds represented by general formula (1) of the present invention exhibit no antiferroelectric liquid crystal phase but can be incorporated into an antiferroelectric liquid crystal or composition thereof having a high threshold voltage to lower the threshold voltage of the resulting composition. Furthermore, two or more of the compounds represented by general formula (1) may be used in admixture.

Moreover, the compound of the present invention exhibits good miscibility with known antiferroelectric liquid crystal compounds, and thus can easily form an antiferroelectric liquid crystal composition when mixed together. Preferred examples of such known antiferroelectric liquid crystal compounds include those terminated by the following groups:

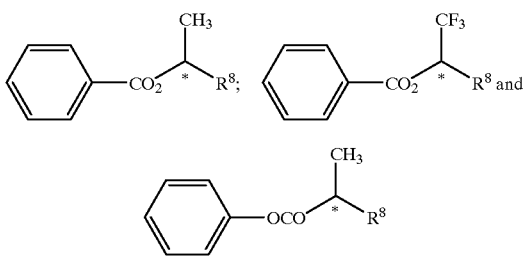

wherein $R^8$ represents a straight-chain alkyl group or an alkyl group having an ether bond.

Particularly preferred examples of the antiferroelectric liquid crystal compound are given below.

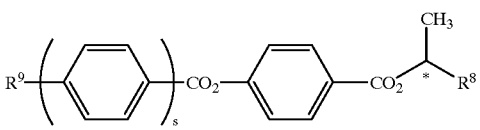

-continued

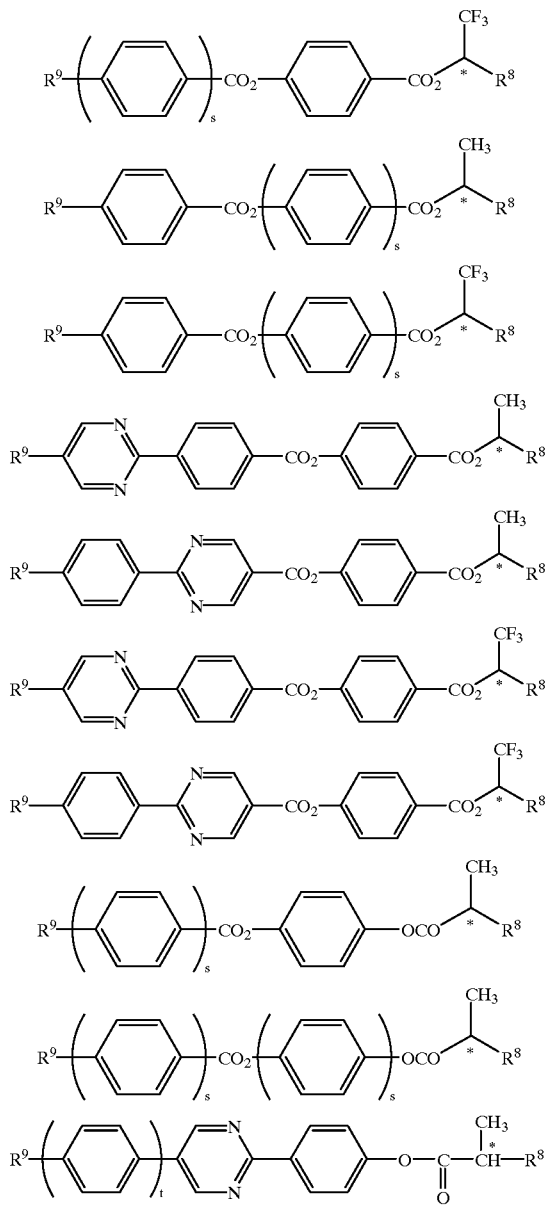

wherein $R^8$ represents a straight-chain alkyl group or an alkyl group having an ether bond; $R^9$ represents an alkyl group or an alkoxy group; s represents 1 or 2; and t represents 0 or 1.

Other examples of the foregoing compound include compounds obtained by substituting some of the hydrogen atoms in the phenylene group in the foregoing general formulae by fluorine atoms.

When the optically active compound represented by general formula (1) of the present invention and the foregoing known antiferroelectric liquid crystal compounds or compositions thereof are mixed to obtain an antiferroelectric liquid crystal composition, the total content of the optically active compound represented by general formula (1) of the present invention is preferably from 1 to 40% by weight.

On the other hand, the optically active compound of the present invention has good miscibility with known compounds which exhibit a smectic C phase or chiral smectic C phase but which do not exhibit an antiferroelectric liquid crystal phase, such as phenylpyrimidine and phenyl benzoate. Therefore, the optically active compound represented by general formula (1) of the present invention can be mixed with such compounds to obtain a ferroelectric liquid crystal composition.

In addition, the resulting ferroelectric liquid crystal composition can be mixed with antiferroelectric liquid compounds or compositions thereof so long as the layer structure of the antiferroelectric liquid crystal phase can be maintained to yield a desired antiferroelectric liquid crystal composition. In this case, the total content of the optically active compound of the present invention and ferroelectric liquid crystal compounds or a composition thereof is preferably from 1 to 40% by weight, more preferably from 1 to 30% by weight of the antiferroelectric liquid crystal composition.

Thus, the optically active compounds of the present invention generally exhibit no antiferroelectric liquid crystal phase but can be mixed with antiferroelectric liquid crystal compounds or their compositions to reduce the threshold voltage of the resulting composition, and can be incorporated into electro-optic elements and other like elements employing an antiferroelectric liquid crystal. Furthermore, the compound of the present invention has good miscibility with many known conventional liquid crystal compounds and thus can provide a liquid crystal material having improved temperature characteristics.

Furthermore, the optically active compound of the present invention can be incorporated into an antiferroelectric liquid crystal compound having a high threshold voltage to lower the threshold voltage of the resulting composition, thus making it possible to obtain an even more desirable antiferroelectric liquid crystal composition.

The optically active compound of the present invention represented by the foregoing general formula (1) can be synthesized, for example, by the following method. For example, optically active 2-fluoroalkanoic acids can be synthesized by fluorinating the corresponding 2-hydroxyalkanoates with a fluorinating agent such as hexafluoropropene diethylamine, followed by hydrolysis.

Moreover, 2-fluoroalkanoic acids can be also obtained by asymmetrically hydrogenating 2-fluoro-2-alkenoic acid. Optically active 2-trifluoromethylalkanoic acids can be obtained by optically resolving the racemates of 2-trifluoromethylalkanoic acids or derivatives thereof with lipase or the like.

Furthermore, optically active 2-trifluoromethylalkanoic acids can also be synthesized with the use of a chiral auxiliary as follows.

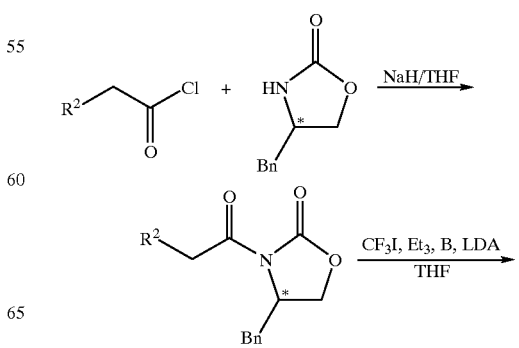

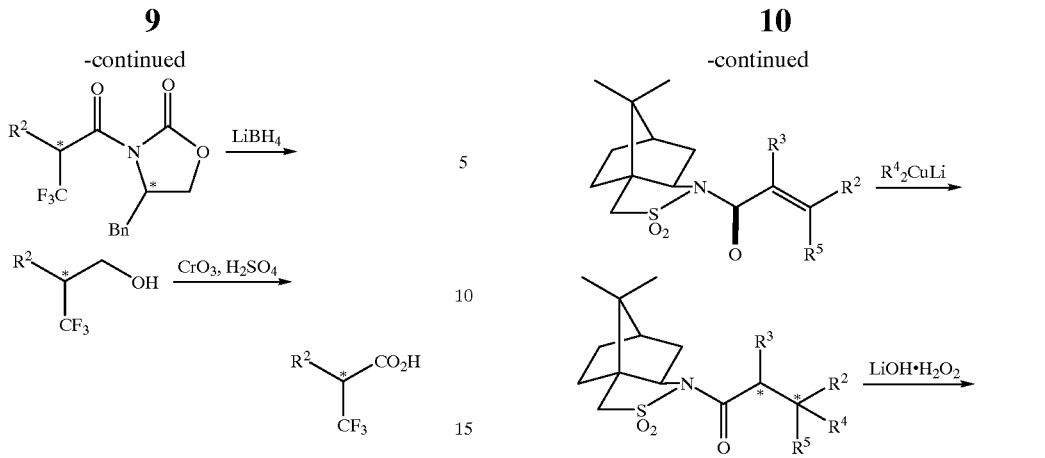

Optically active 2-fluoro-2-trifluoromethylalkanoic acids can be obtained by optically resolving with the chiral auxiliary described above, and can also be synthesized using the following novel process. Thus, optically active 2-fluoro-2-trifluoromethylalkanoic acids can be prepared by reacting an optically active 1-substituted allylalcohol with hexafluoropropene diethylamine.

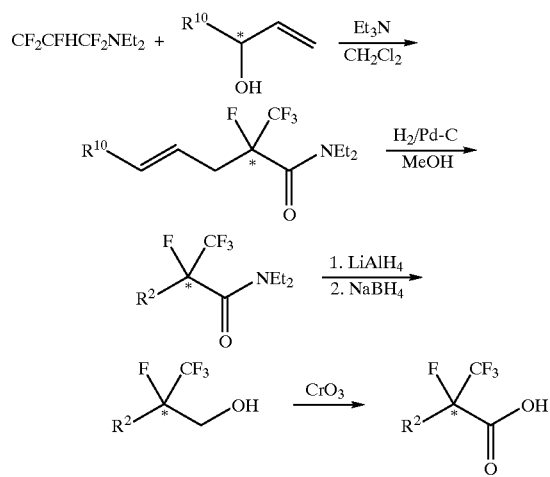

In this reaction scheme, $R^{10}$ is an alkyl group having 1 to 9 carbon atoms and $R^2$ is an alkyl group having 4 to 12 carbon atoms. Furthermore, 2,3-dialkylcarboxylic acids can be prepared with a chiral sultam as shown in the following reaction scheme.

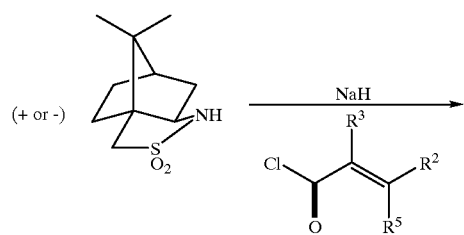

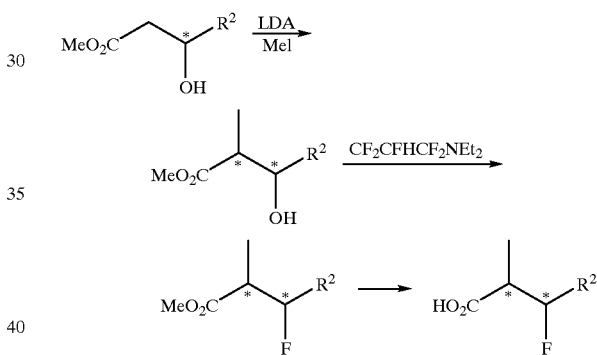

In addition, 2-methyl-3-fluoroalkanoic acids can be synthesized from optically active β-hydroxyacids obtained by asymmetric hydrogenation of β-ketoacids as follows.

Optically active 1,1,1-trifluoro-2-alkanols can be optically resolved from the corresponding racemates with lipase.

The core moiety of the compound of the present invention can be synthesized by an ordinary method. The compounds of the present invention can be obtained from the core moiety by condensing with 2-substituted alkanoic acids or with 2-alkanols.

A method for synthesizing the compound represented by general formula (1) when D is —OCO— or —OCOC*$R^3$H— is described below. Firstly, a diphenylpyrimidine derivative is obtained from a perchlorate derivative of (3-dimethylamino-2-(4-alkyl or 4-alkoxyphenyl) propenylidene)dimethyl ammonium and a p-hydroxybenzamidine hydrochloride by a conventional method. The diphenylpyrimidine derivative thus prepared is then subjected to ordinary esterification with the foregoing optically active alkanoic acids to obtain the desired compound. An example of this synthesis route is given below.

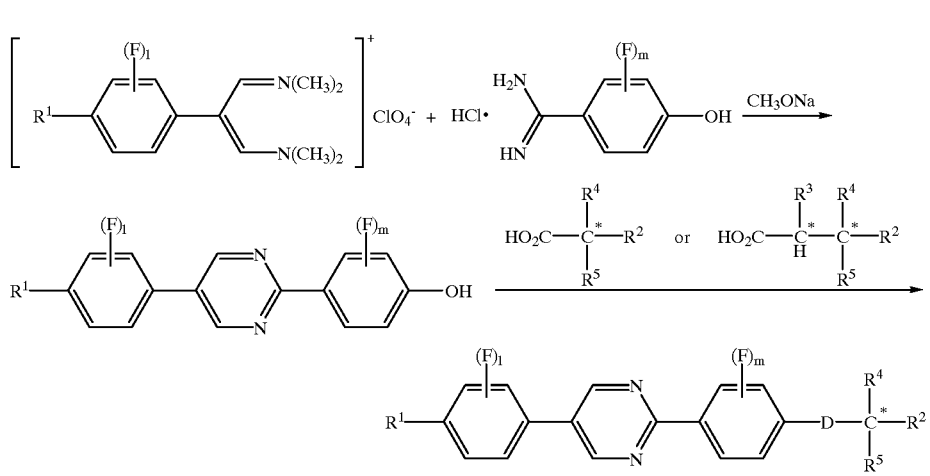

A method for synthesizing the compound represented by general formula (1) when D is —CH$_2$—O— is described below. The diphenylpyrimidine derivative prepared in a similar manner as described above is reduced to hydroxymethyl one. After conversion of the hydroxymethyl group into a chloromethyl group, the chloromethyl derivative is reacted with the foregoing optically active alcohol to obtain the desired compound. The reaction scheme of this synthetic route is given below.

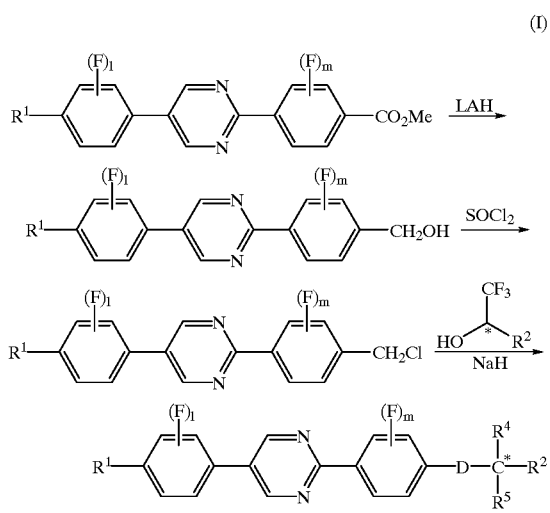

EXAMPLES

The present invention is described in further detail by reference to the following Examples, however, the present invention should not be construed as being limited thereto. The phase transition temperature in the following Examples was determined by visual observation under a polarizing microscope equipped with a hot stage and by measuring with a differential scanning calorimeter (DSC). The identification of various liquid crystal phases was carried out by a so-called miscibility test and contact method well known to the skilled artisan.

For the evaluation of various liquid crystal compounds and compositions, a liquid crystal evaluation cell was employed. The evaluation cell was prepared by providing a transparent conductive film (indium tin oxide: ITO) on two glass sheet substrates, coating these glass substrates with an oriented film made of a polyimide, polyvinyl alcohol or the like, rubbing the glass substrates, and then laminating the glass substrates in such manner that the rubbing directions were parallel to each other. The cell thus prepared had a gap of 2.3 μm.

For measuring electro-optic effects such as threshold voltage, a temperature-controlled liquid crystal cell disposed between a polarizer and an analyzer in a crossed Nicols arrangement was irradiated with a He—Ne laser. Under these conditions, the response of the liquid crystal to an applied voltage was determined by observing the change in transmittance measured by a photo-electron multiplier. The threshold voltage is defined as the voltage required to provide a transmittance of 90% assuming that the dark level corresponds to a transmittance of 0% and the bright level corresponds to a transmittance of 100% under application of a triangular wave. The term "Tc" as used herein is the upper temperature limit for an antiferroelectric liquid crystal phase.

Example 1

Synthesis of 5-(3-fluoro-4-octyloxyphenyl)-2-(3-fluoro-4-((S)-2-fluoroheptanoyloxy)phenyl)-1,3-pyrimidine Into a reaction flask were charged 0.77 g of 5-(3-fluoro-4-octyloxyphenyl)-2-(3-fluoro-4-hydroxyphenyl)-1,3-pyrimidine, 0.41 g of (S)-2-fluoroheptanoic acid, 0.86 g of dicyclohexylcarbodiimide (DCC), 116 mg of dimethylaminopyridine (DMAP) and 40 ml of 1,2-dichloroethane in a stream of nitrogen. The mixture was then stirred for 3 hours at room temperature. After filtering the resulting salt, the filtrate was evaporated to dryness. The raw product obtained was purified by silica gel column chromatography (toluene:ethyl acetate=10:1) and then by medium pressure liquid chromatography to obtain 0.88 g of the desired compound (yield: 87.3%).

$^1$H-NMR(CDCl$_3$)δ: 0.90 (t, 3H, J=7.0 Hz), 0.94 (t, 3H, J=7.2 Hz), 1.26– 1.42 (m, 12H), 1.45–1.53 (m, 2H), 1.57–1.63 (m, 2H), 1. 82–1.90 (m, 2H), 2.03–2.20 (m, 2H), 4.10 (t, 2H, J=6.6 Hz), 5.23 (dt, 1H, J=48.7 Hz, J=5.9 Hz), 7.10 (t, 1H, J=8.5 Hz), 7.26–7.39 (m, 3H), 8.31–8.36 (m, 2H), 8.95 (s, 2H)

MS(m/z): 542 (M$^+$)

This compound melted and changed to a ferroelectric liquid crystal phase (SmC* phase) at a temperature of 81.3° C. and then to an isotropic phase at 140.7° C.

Reference Example 1

Synthesis of 5-(4-decylphenyl)-2-(4-((S)-2,6,-dimethylheptanoyloxy)phenyl)-1,3-pyrimidine The procedure of Example 1 was followed, except that 5-(3-fluoro-4-octyloxyphenyl)-2-(3-fluoro-4-hydroxy) phenyl)-1,3-pyrimidine was replaced by 5-(4-decylphenyl)-2-(4-hydroxyphenyl)-1,3-pyrimidine and (S)-2-fluoroheptanoic acid was replaced by (S)-2,6-dimethylheptanoic acid. Thus, 5-(4-decylphenyl)-2-(4-((S)-2,6,-dimethylheptanoyloxy)phenyl)-1,3-pyrimidine was prepared.

This compound melted to provide an antiferroelectric liquid crystal phase at 100.7° C., and changed to an isotropic phase at 131.7° C. This compound was injected into a liquid crystal cell and its threshold voltage was measured at a temperature of 116.7° C. (Tc-15° C.). The measured threshold voltage was 59 V.

Example 2

To the compound of Reference Example 1 was added the compound of Example 1 in an amount of 10.1% by weight to obtain a liquid crystal composition. This composition changed from an isotropic phase to a SmC* phase at 129.4° C. and then exhibited an antiferroelectric liquid crystal phase at 128.9° C. (Tc). The antiferroelectric liquid crystal composition thus obtained was injected into a liquid crystal cell and its threshold voltage was measured at a temperature of (Tc-15° C.). The measured threshold voltage was 38.4 V. The compound of Reference Example 1 had a threshold voltage of 59 V at a temperature of (Tc-15° C.). Thus, it can be seen that incorporation of the compound of Example 1 reduced the threshold voltage of the resulting composition, thus making it possible to obtain a stable antiferroelectric liquid crystal composition having improved properties.

Example 3

Synthesis of 5-(4-octylphenyl)-2-(3-fluoro-4-((S)-2-fluoroheptanoyloxy)phenyl)-1,3-pyrimidine The procedure of Example 1 was followed, except that 5-(3-fluoro-4-octyloxyphenyl)-2-(3-fluoro-4-hydroxy) phenyl)-1,3-pyrimidine was replaced by 5-(4-octylphenyl)-2-(3-fluoro-4-hydroxyphenyl)-1,3-pyrimidine. Thus, the aboved-titled compound was obtained.

$^1$H-NMR(CDCl$_3$)δ: 0.89 (t, 3H, J=7.0 Hz), 0.94 (t, 3H, J=7.1 Hz), 1.26–1.42 (m, 14H), 1.58–1.70 (m, 4H), 2.03–2.14 (m, 2H), 2.68 (t, 2H, J=7.8 Hz), 5.23 (dt, 1H, J=48.8 Hz, J=5.9 Hz), 7.30 (m, 1H), 7.35 (d, 2H, J=8.3 Hz), 7.55 (d, 2H, J=8.3 Hz), 8.32–8.37 (m, 2H), 9.00 (s, 2H)

MS(m/z): 508 (M$^+$)

This compound melted to provide a ferroelectric liquid crystal phase (SmC* phase) at a temperature of 89.9° C., exhibited a smectic A (SmA) phase at 140° C., and then changed to an isotropic phase at 165° C. When this compound was added to the compound of Reference Example 1 in an amount of 10.0% by weight, a liquid crystal composition was obtained. This composition changed from an isotropic phase to a smectic A phase at a temperature of 129.5° C., exhibited a SmC* phase at a temperature of 129.3° C., and then changed to an antiferroelectric liquid crystal phase at a temperature of 128° C. (Tc). This antiferroelectric liquid crystal composition was injected into a liquid crystal cell, and the threshold voltage was then measured at a temperature of (Tc-15° C.). The measured threshold voltage was 40.8 V. The compound of Reference Example 1 had a threshold voltage of 59 V at a temperature of (Tc-15° C.). Thus, it can be seen that incorporation of the compound of Example 3 reduced the threshold voltage of the resulting composition, thus making it possible to obtain a stable antiferroelectric liquid crystal composition having improved properties.

Example 4

Synthesis of 5-(4-octyloxyphenyl)-2-(4-((S)-2-fluoroheptanoyloxy)phenyl)-1,3-pyrimidine The procedure of Example 1 was followed, except that 5-(3-fluoro-4-octyloxyphenyl)-2-(3-fluoro-4-hydroxy) phenyl)-1,3-pyrimidine was replaced by 5-(4-octyloxyphenyl)-2-(4-hydroxyphenyl)-1,3-pyrimidine. Thus, the above-titled compound was obtained.

$^1$H-NMR(CDCl$_3$)δ: 0.90 (t, 3H, J=7.0 Hz), 0.94 (t, 3H, J=7.1 Hz), 1.26–1.42 (m, 12H), 1.45–1.52 (m, 2H), 1.57–1.63 (m, 2H), 1.79–1.86 (m, 2H), 2.02–2.15 (m, 2H), 4.02 (t, 2H, J=6.6 Hz), 5.17 (dt, 1H, J=48.8 Hz, J=5.9 Hz), 7.05 (d, 2H, J=8.8 Hz), 7.27 (d, 2H, J =8.8 Hz), 7.56 (d, 2H, J=8.9 Hz), 8.53 (d, 2H, J=8.9 Hz), 8.97 (s, 2H)

MS(m/z): 506 (M$^+$)

This compound melted to provide an unidentified high order smectic phase at 124.6° C., changed to another unidentified high order smectic phase at 132.2° C., exhibited a SmC* phase at 139.6° C., changed to a SmA phase at 180.9° C., and then to an isotropic phase at 205° C. When this compound was added to the compound of Reference Example 1 in an amount of 20.0% by weight, a liquid crystal composition was obtained. This composition changed from an isotropic phase to a smectic A phase at 140.4° C., exhibited a SmC* phase at 139.1° C., and then changed to an antiferroelectric liquid crystal phase at a temperature of 129.7° C. (Tc). The antiferroelectric liquid crystal composition thus obtained was injected into a liquid crystal cell, and the threshold voltage was measured at a temperature of (Tc-15° C.). The measured threshold voltage was 30 V. The compound of Reference Example 1 had a threshold voltage of 59 V at a temperature of (Tc-15° C.). Thus, it can be seen that incorporation of the compound of Example 4 in an amount of 20% by weight also reduced the threshold voltage of the resulting composition, thus making it possible to obtain a stable antiferroelectric liquid crystal composition having improved properties.

Example 5

Synthesis of 5-(4-decylphenyl)-2-(4-((S)-2-trifluoromethyloctanoyloxy)phenyl)-1,3-pyrimidine The procedure of Example 1 was followed, except that 5-(3-fluoro-4-octyloxyphenyl)-2-(3-fluoro-4-hydroxy) phenyl)-1,3-pyrimidine was replaced by 5-(4-decylphenyl)-2-(4-hydroxyphenyl)-1,3-pyrimidine and (S)-2-fluoroheptanoic acid was replaced by (S)-2-trifluoromethyloctanoic acid. Thus, the desired compound was obtained.

$^1$H-NMR(CDC$_{13}$)δ: 0.88 (t, 3H, J=6.9 Hz), 0.91 (t, 3H, J=6.9 Hz), 1.22–1.60 (m, 22H), 1.62–1.70 (m, 2H), 1.88–1.98 (m, 1H), 2.02–2.15 (m, 1H), 2.68 (t, 2H, J=7.7 Hz), 3.32–3.43 (m, 1H), 7.24 (d, 2H, J =8.9 Hz), 7.34 (d, 2H, J=8.3 Hz), 7.55 (d, 2H, J=8.3 Hz), 8.55 (d, 2H, J=8.9 Hz), 9.01 (s, 2H)

MS(m/z): 582 (M$^+$)

This compound melted to exhibit an unidentified high order smectic phase at a temperature of 60.6° C., and then assumed an isotropic phase at a temperature of 80.7° C. When this compound was added to the compound of Reference Example 1 in an amount of 9.5% by weight, a liquid crystal composition was obtained. This composition had an antiferroelectric liquid crystal phase upper temperature limit (Tc) of 123.7° C. The antiferroelectric liquid crystal composition thus obtained was injected into a liquid crystal cell, and the threshold voltage was measured at a temperature of (Tc-15° C.). The measured threshold voltage was 40.8 V. The compound of Reference Example 1 had a threshold voltage of 59 V at a temperature of (Tc-15° C.). Thus, it can be seen that incorporation of the compound of Example 5 reduced the threshold voltage of the resulting composition, thus making it possible to obtain a stable antiferroelectric liquid crystal composition having improved properties.

Example 6
Synthesis of 5-(4-decylphenyl)-2-(3-fluoro-4-((R)-2-trifluoromethyloctanoyloxy)pheny)-1,3-pyrimidine The procedure of Example 5 was followed, except that 5-(4-decylphenyl)-2-(4-hydroxyphenyl)-1,3-pyrimidine was replaced by 5-(4-decylphenyl)-2-(3-fluoro-4-hydroxyphenyl)-1,3-pyrimidine and (S)-2-trifluoromethyloctanoic acid was replaced by (R)-2-trifluoromethyloctanoic acid. Thus, the desired compound was obtained.

$^1$H-NMR(CDCl$_3$)δ: 0.88 (t, 3H, J=6.9 Hz), 0.91 (t, 3H, J=7.0 Hz), 1.20–1.68 (m, 22H), 1.70–1.72 (m, 2H), 1.88–1.98 (m, 1H), 2.02–2.16 (m, 1H), 2.68 (t, 2H, J=7.7 Hz), 3.38–3.48 (m, 1H), 7.25–7.28 (m, 1H), 7.35 (d, 2H, J=8.4 Hz), 7.55 (d, 2H, J=8.4 Hz), 8.32–8.37 (m, 2H), 9.00 (s, 2H)

MS(m/z): 600 (M$^+$)

This compound melted to provide an unidentified high order smectic phase at a temperature of 52° C. and then became an isotropic phase at a temperature of 71° C.

Example 7
Synthesis of 5-(4-decyloxyphenyl)-2-(4((R)-2-trifluoromethyloctanoyloxy)phenyl)-1.3-pyrimidine The procedure of Example 6 was followed, except that 5-(4-decylphenyl)-2-(3-fluoro-4-hydroxyphenyl)-1,3-pyrimidine was replaced by 5-(4-decyloxyphenyl)-2-(4-hydroxyphenyl)-1,3-pyrimidine. Thus, the desired compound was obtained.

$^1$H-NMR(CDCl$_3$)δ: 0.89 (t, 3H, J=6.9 Hz), 0.91 (t, 3H, J=7.1 Hz), 1.20–1.60 (m, 22H), 1.78–1.87 (m, 2H), 1.88–1.98 (m, 1H), 2.02–2.15 (m, 1H), 3.32–3.42 (m, 1H), 4.02 (t, 2H, J=6.6 Hz), 7.05 (d, 2H, J=8.9 Hz), 7.24 (d, 2H, J=8.9 Hz), 7.56 (d, 2H, J 8.8 Hz), 8.54 (d, 2H, J=9.0 Hz), 8.98 (s, 2H)

MS(m/z): 598 (M$^+$)

This compound melted to exhibit an unidentified high order smectic phase at 69° C. and then an isotropic phase at 106° C.

Reference Example 2
Synthesis of 5-(4-decylphenyl)-2-(4-((R)-2,6,-dimethylheptanoyloxy)phenyl)-1,3-pyrimidine The procedure of Reference Example 1 was followed, except that (S)-2,6-dimethylheptanoic acid was replaced by (R)-2,6-dimethylheptanoic acid. Thus, 5-(4-decylphenyl)-2-(4-((R)-2,6,-dimethylheptanoyloxy)phenyl)-1,3-pyrimidine was prepared.

This compound melted to provide an antiferroelectric liquid crystal phase at 100° C. and changed to an isotropic phase at 128° C. This compound was injected into a liquid crystal cell and the threshold voltage was measured at a temperature of 113° C. Tc-15° C.). The measured threshold voltage was 51.2 V.

Example 8
To the compound shown in Reference Example 2 was added the compound of Example 7 in an amount of 30.1% by weight and a liquid crystal composition was obtained. This composition changed from an isotropic phase to a SmA phase at 127° C., changed to a SmC* phase at 113° C., and then exhibited an antiferroelectric liquid crystal phase at 109° C. (Tc). The antiferroelectric liquid crystal composition thus obtained was injected into a liquid crystal cell and the threshold voltage was measured at a temperature of (Tc-15° C.). The measured threshold voltage was 19.2 V. The compound of Reference Example 2 had a threshold voltage of 51.2 V at a temperature of (Tc-15° C.). Thus, it can be seen that incorporation of the compound of Example 7 in an amount of 30% by weight reduced the threshold voltage of the resulting composition, thus making it possible to obtain a stable antiferroelectric liquid crystal composition having improved properties.

Example 9
Synthesis of 5-(4-decylphenyl)-2-(4-((R)-1-trifluoromethylheptyloxymethyl)phenyl)-1,3-pyrimidine (1) Synthesis of 5-(4-decylphenyl)-2-(4-hydroxymethylphenyl)-1,3-pyrimidine Into a reaction flask were charged 1.2 g of lithium aluminium hydride (LAH) and 50 ml of THF in a stream of nitrogen. Into the mixture was added dropwise a THF (250 ml) solution of 5-(4-decylphenyl)-2-(4-ethoxycarbonylphenyl)-1,3-pyrimidine (9.1 g), keeping the temperature within a range of from 5 to 15° C.

The reaction mixture was stirred for another 2 hours at room temperature, poured into water, and extracted with ethyl acetate. The organic layer was separated, washed with water, and evaporated to dryness. The raw material thus obtained was purified by silica gel column chromatography and recrystallized from hexane to obtain 4.12 g of the desired compound (Yield: 48.4%).

(2) Synthesis of 5-(4-decylphenyl)-2-(4-chloromethylphenyl)-1,3-pyrimidine

Into a reaction flask were added 1.32 g of 5-(4-decylphenyl)-2-(4-hydroxymethylphenyl)-1,3-pyrimidine, 1.54 g of thionyl chloride and 20 ml of methylene chloride. The reaction mixture was maintained at 75° C. for 3 hours with stirring.

The mixture was poured into water, extracted with ethyl acetate, washed with water and then concentrated. The resulting raw product was purified by silica gel column chromatography (benzene-ethyl acetate) to obtain 1.30 g of the desired compound (Yield: 94.2%).

(3) Synthesis of 5-(4-decylphenyl)-2-(4-((R)-1-trifluoromethylheptyloxymethyl)phenyl)-1,3-pyrimidine Under nitrogen, 0.35 g of (R)-1, 1, 1-trifluoro-2-octanol in THF (2 ml) was added to a dispersion prepared from 0.8 g of 5-(4-decylphenyl)-2-(4-chloromethylphenyl)-1,3-pyrimidine, 10 ml of THF and 0.1 g of NaH. The mixture was stirred at 65° C. for 1 hour and for an additional 2 hours at 75° C. After cooling, the resulting mixture was poured into a large amount of water, extracted with ethyl acetate, washed with water and then concentrated to obtain a raw product. This product was purified with silica gel column chromatography (hexane-ethyl acetate), and further purified by recrystallization from acetonitrile to obtain 0.55 g of the desired material (Yield: 50.9%).

$^1$H-NMR(CDCL$_3$)δ: 0.85 (t, 3H, J=6.8 Hz), 0.88 (t, 3H, J=6.9 Hz), 1.20–1.40 (m, 22H), 1.60–1.78 (m, 4H), 2.68 (t, 2H, J=7.7 Hz), 3.68–3.78 (m, 1H), 4.66 (d, 1H, J=11.7 Hz), 4.93 (d, 1H, J=11.7 Hz), 7.34 (d, 2H, J=8.3 Hz), 7.48 (d, 2H, J=8.3 Hz), 7.55 (d, 2H, J=8.3 Hz), 8.49 (d, 2H, J =8.4 Hz), 9.01 (s, 2H)

MS(m/z): 568 (M$^+$)

This compound melted and changed to an isotropic phase at 75.1° C. On cooling, a monotropic SmA phase was observed. The phase transition temperature from a SmA phase to an isotropic phase was 74.3° C. This compound was added to the compound of Reference Example 1 in an amount of 20.1% by weight to obtain a liquid crystal composition. This composition changed from an isotropic phase to a SmA phase at 119° C., showed a SmC* phase at 114.9° C., and then exhibited an antiferroelectric liquid crystal phase at 112.9° C. The antiferroelectric liquid crystal composition thus obtained was injected into a liquid crystal cell, and the measured threshold voltage of the composition was 20.4 V at a temperature of (Tc-15° C.). The compound of Reference Example 1 had a threshold voltage of 59 V at a temperature of (Tc-15° C.). Thus, it can be seen that incorporation of the compound of Example 9 in an amount of 20% reduced the threshold voltage of the resulting composition, thus making it possible to obtain a stable antiferroelectric liquid crystal composition having improved properties.

Example 10
Synthesis of 5-(-4-octylphenyl)-2-(4-((R)-1-trifluoromethylheptyloxymethyl)phenyl)-1,3-pyrimidine The procedure of Example 9 was followed, except that 5-(4-decylphenyl)-2-(4-ethoxycarbonylphenyl)-1,3-pyrimidine was replaced by 5-(4-octylphenyl)-2-(4-methoxycarbonylphenyl)-1,3-pyrimidine in step (1) of Example 9. Thus, the above-titled compound was obtained.

$[\alpha]_D^{25}$=+36.8°(c=1.05, CHCl$_3$).

$^1$H-NMR(CDCl$_3$)δ: 0.85 (t, 3H, J=7.0 Hz), 0.89 (t, 3H, J=6.9 Hz), 1.19– 1.42 (m, 16H), 1.48–1.58 (m, 2H), 1.6–1.75 (m, 4H), 2.68 (t, 2H, J=7.7 Hz), 3.66–3.76 (m, 1H), 4.66 (d, 1H, J=11.8 Hz), 4.93 (d, 1H, J=11.7 Hz), 7.34 (d, 2H, J =8.3 Hz), 7.49 (d, 2H, J=8.5 Hz), 7.55 (d, 2H, J=8.3 Hz), 8.49 (d, 2H, J=8.4 Hz), 9.01 (s, 2H)
MS(m/z): 540 (M$^+$)

This compound melted to provide a SmA phase at 68.5° C., and changed to an isotropic phase at 81.9° C. This compound was added to the compound of Reference Example 1 in an amount of 9.9% by weight to obtain a liquid crystal composition. This composition changed from an isotropic phase to a SmA phase at 124.1° C., and then exhibited an antiferroelectric liquid crystal phase at 122.6° C. The antiferroelectric liquid crystal composition thus obtained was injected into a liquid crystal cell, and the measured threshold voltage of the composition was 45.2 V at a temperature of (Tc-15° C.). The compound of Reference Example 1 had a threshold voltage of 59 V at a temperature of (Tc-15° C.). Thus, it can be seen that incorporation of the compound of Example 10 reduced the threshold voltage of the resulting composition, thus making it possible to obtain a stable antiferroelectric liquid crystal composition having improved properties.

Example 11
Synthesis of 5-(4-decyloxyphenyl)-2-(4-((R)-1-trifluoromethylheptyloxymethyl)phenyl)-1,3-pyrimidine The above-titled compound was synthesized in the same manner as in Example 9, except for replacing the 5-(4-decylphenyl)-2-(4-ethoxycarbonylphenyl)-1,3-pyrimidine used in Example 9-(1) with 5-(4-decyloxyphenyl)-2-(4-methoxycarbonylphenyl)-1,3-pyrimidine.

$[\alpha]_D^{25}$=+34.6°(c=1.15, CHCl$_3$).

$^1$H-NMR(CDCl$_3$)δ: 0.85 (t, 3H, J=6.9 Hz), 0.89 (t, 3H, J=6.9 Hz), 1.20–1.43 (m, 20H), 1.43–1.57 (m, 2H), 1.60–1.73 (m, 2H), 1.76–1.85 (m, 2H), 3.67–3.77 (m, 1H), 4.02 (t, 2H, J=6.6 Hz), 4.66 (d, 1H, J=11.8 Hz), 4.93 (d, 1H, J=11.7 Hz), 7.05 (d, 2H, J=8.9 Hz), 7.49 (d, 2H, J=8.5 Hz), 7.56 (d, 2H, J =8.9 Hz), 8.48 (d, 2H, J=8.5 Hz), 8.98 (s, 2H)
MS(m/z): 584 (M$^+$)

This compound melted at 65.3° C. to provide a SmC* phase, and changed to a SmA phase at 74.9° C., then to an isotropic phase at 101.1° C. This compound was added to the compound of Reference Example 1 in an amount of 10.0% to obtain a liquid crystal composition. This composition changed from an isotropic phase to a SmA phase at 124.2° C., and then exhibited an antiferroelectric liquid crystal phase at 123.6° C. (Tc). The antiferroelectric liquid crystal composition thus obtained was injected into a liquid crystal cell and the threshold voltage was measured at Tc-15° C. The measured threshold voltage of the composition was 36 V. The compound of Reference Example 1 had a threshold voltage of 59 V at a temperature of (Tc-15° C.). Thus, it can be seen that incorporation of the compound of Example 11 reduced the threshold voltage of the resulting composition, thus making it possible to obtain a stable antiferroelectric liquid crystal composition having improved properties.

Example 12
Synthesis of 5-(4-decylphenyl)-2-(4-((R)-1-trifluoromethylpentyloxymethyl)phenyl)-1,3-pyrimidine The synthetic procedure of Example 9 was followed, except for replacing (R)-1,1, 1-trifluoro-2-octanol used in step (3) of Example 9 with (R)-1,1,1-trifluoro-2-hexanol to obtain the above-titled compound.

$^1$H-NMR(CDCl$_3$)δ ppm: 0.88 (t, 3H, J=6.9 Hz), 0.89 (t, 3H, J=7.0 Hz), 1.20–1.43 (m, 16H), 1.45–1.58 (m, 2H), 1.60–1.75 (m, 4H), 2.68 (t, 2H, J=6.7 Hz), 3.67–3.77 (m, 1H), 4.66 (d, 1H, J=11.8 Hz), 4.92 (d, 1H, J=11.8 Hz), 7.34 (d, 2H, J=8.4 Hz), 7.49 (d, 2H, J=8.4 Hz), 7.54 (d, 2H, J=8.4 Hz), 8.49 (d, 2H, J=8.4 Hz), 9.01 (s, 2H)
MS(m/z): 540 (M$^+$)

This compound melted at 68.1° C., at which it exhibited a SmA phase, and then changed to an isotropic phase at 87.8° C. In addition, when this compound was cooled from a SmA phase it exhibited a SmC* phase at 64.6° C.

This compound was added in an amount of 10.0% by weight to the compound of Reference Example 1 to obtain a liquid crystal composition. This composition changed from an isotropic phase at 124.1° C. to a SmA phase, and then exhibited an antiferroelectric liquid crystal phase at 123.4° C. (Tc).

The resulting antiferroelectric liquid crystal composition was injected into a liquid crystal cell, and the measured threshold voltage was 34.4 V at Tc-15° C. The compound of Reference Example 1 had a threshold voltage of 59 V at a temperature of (Tc-15° C.). Thus, it can be seen that incorporation of the compound of Example 12 reduced the threshold voltage of the resulting composition, thus making it possible to obtain a stable antiferroelectric liquid crystal composition having improved properties.

Example 13
Synthesis of 5-(3-fluoro-4-octyloxyphenyl)-2-(4-((R)-1-trifluoromethylheptyloxymethyl)phenyl)-1,3-pyrimidine The above-titled compound was synthesized in the same manner as in Example 9, except for replacing 5-(4-decylphenyl)-2-(4-ethoxycarbonylphenyl)-1,3-pyrimidine used in step (1) with 5-(3-fluoro-4-octyloxyphenyl)-2-(4-methoxycarbonylphenyl)-1,3 -pyrimidine.

$^1$H-NMR(CDCl$_3$)δ: 0.86 (t, 3H, J=6.9 Hz), 0.90 (t, 3H, J=7.0 Hz), 1.21–1.42 (m, 16H), 1.45–1.57 (m, 2H), 1.62–1.76 (m, 2H), 1.82–1.92 (m, 2H), 3.67–3.78 (m, 1H), 4.10 (t, 2H, J=6.7 Hz), 4.66 (d, 1H, J=11.7 Hz), 4.93 (d, 1H, J=11.7 Hz), 7.10 (t, 1H, J=8.6 Hz), 7.32–7.39 (m, 2H), 7.49 (d, 2H, J=8.6 Hz), 8.48 (d, 2H, J=8.5 Hz), 8.96 (s, 2H)

MS(m/z): 574 (M$^+$)

This compound melted at 72.7° C. to provide a SmA phase, and changed to an isotropic phase at 77.3° C. This compound was added to the compound of Reference Example 1 in an amount of 20.0% by weight to obtain a liquid crystal composition. The composition changed from an isotropic phase at 121.7° C. to a SmA phase, and exhibited an antiferroelectric liquid crystal phase at 121° C. The antiferroelectric liquid crystal composition was injected into a liquid crystal cell and the measured threshold voltage was 34.8 V at Tc-15° C. The compound of Reference Example 1 had a threshold voltage of 59 V at a temperature of (Tc-15° C.). Thus, it can be seen that incorporation of the compound of Example 13 reduced the threshold voltage of the resulting composition, thus making it possible to obtain a stable antiferroelectric liquid crystal composition having improved properties.

Example 14

Synthesis of 5-(4-decylphenyl)-2-(3-fluoro-4-((R)-1-trifluoromethylheptyloxymethyl)phenyl)-1,3-pyrimidine The synthetic procedure of Example 9 was followed, except for replacing 5-(4-decylphenyl)-2-(4-ethoxycarbonylphenyl)-1,3-pyrimidine used in step (1) with 5-(4-decylphenyl)-2-(3-fluoro-4-methoxycarbonylphenyl)-1,3-pyrimidine to obtain the above-titled compound.

$^1$H-NMR(CDCl$_3$)δ: 0.85 (t, 3H, J=7.0 Hz), 0.88 (t, 3H, J=7.1 Hz), 1.18–1.43 (m, 20H), 1.46–1.58 (m, 2H), 1.60–1.75 (m, 4H), 2.68 (t, 2H, J=7.8 Hz), 3.68–3.80 (m, 1H), 4.76 (d, 1H, J=11.9 Hz), 4.94 (d, 1H, J=12.1 Hz), 7.35 (d, 2H, J=8.3 Hz), 7.54–7.58 (m, 3H), 8.20 (dd, 1H, J=11.2 Hz, J=1.6 Hz), 8.30 (dd, 1H, J=8.0 Hz, J=1.6 Hz), 9.01 (s, 2H)

MS(m/z): 587 (M$^+$+1)

This compound melted at 60.3° C. to provide an isotropic phase, but on cooling, a monotropic SmC* phase was observed. The phase transition temperature from a SmC* phase to an isotropic phase was 48.1° C.

This compound was added in an amount of 10.0% by weight to the compound of Reference Example 1 to obtain the liquid crystal composition. This composition changed from an isotropic phase at 122.1° C. to a SmA phase and then exhibited an antiferroelectric liquid crystal phase at 120.0° C. (Tc).

The resulting antiferroelectric liquid crystal composition was injected into a liquid crystal cell, and the measured threshold voltage was 40 V at Tc-20° C. The compound of Reference Example 1 had a threshold voltage of more than 60 V at a temperature of (Tc-20° C.). Thus, it can be seen that incorporation of the compound of Example 14 reduced the threshold voltage of the resulting composition, thus making it possible to obtain a stable antiferroelectric liquid crystal composition having improved properties.

Example 15

Synthesis of 5-(4-decylphenyl)-2-(4-((R)-2-fluoro-2-trifluoromethyloctanoyloxy)phenyl)-1,3-pyrimidine (1) Synthesis of (R)-2-fluoro-2-trifluoromethyloctanoic acid (1-1) Synthesis of 2-fluoro-2-trifluoromethyl-4-octenamide Into a reaction flask were charged 920 mg of (R)-1-hexen-3-ol (91.2%e.e.), 5.7 ml of triethylamine and 10 ml of dichloromethane, and the reaction mixture was cooled to 0° C. Holding the temperature at 0° C., 3.3 ml of hexafluoropropene diethylamine was added dropwise into the mixture. After the addition, the reaction mixture was stirred for 2 hours at 0° C. and 48 hours at room temperature. Into the mixture was added a saturated aqueous solution of sodium bicarbonate, and the mixture was extracted with dichloromethane. The organic layer was dried with anhydrous magnesium sulphate and then concentrated. The raw product was purified by silica gel column chromatography to obtain 1.35 g of the desired compound.

$^1$H-NMR(CDCl$_3$)δ: 0.89 (t, 3H, J=7.1 Hz), 1.15 (t, 3H, J=7.1 Hz), 1.19 (t, 3H, J=6.8 Hz), 1.38 (dt, 2H, J=7.4 Hz, J=14.5 Hz), 1.99 (m, 2H), 2.61 (m, 1H), 3.07 (m, 1H), 3.29–3.60 (m, 2H), 5.33 (dt, 1H, J=7.3 Hz, J=15.3 Hz), 5.68 (dt, 1H, J=6.8 Hz, J=15.3 Hz).

MS(m/z): 283 (M$^+$), 220, 149.

(1-2) Synthesis of 2-fluoro-2-trifluoromethyloctanamide

Into a solution of 1.30 g of 2-fluoro-2-trifluoromethyl-4-octenamide in 13 ml of methanol, palladium-carbon (13 mg) was added under nitrogen. After the atmosphere was replaced with hydrogen, the mixture was stirred for 24 hours. To remove the catalyst, the resulting mixture was filtered with celite and the filtrate was concentrated. The raw product was purified by silica gel column chromatography to obtain 1.0 g of the desired compound.

$^1$H-NMR(CDCl$_3$)δ: 0.89 (t, 3H, J=7.0 Hz), 1.17 (t, 3H, J=7.1 Hz), 1.21 (t, 3H, J=7.0 Hz), 1.24–1.55 (m, 8H), 1.92 (m, 1H), 2.38 (m, 1H), 3.29–3.70 (m, 4H).

MS(m/z): 285 (M$^+$), 270, 256.

(1-3) Synthesis of (R)-2-fluoro-2-trifluoromethyloctanoic acid

Into the suspension of lithium aluminium hydride (67 mg, 1.80 mmol) in tetrahydrofuran (7.0 ml) was slowly added a solution of 1.0 g of 2-fluoro-2-trifluoromethyloctanamide (3.51 mmol) in 3.0 ml of tetrahydrofuran at −20° C. and the reaction mixture was stirred for 6 hours at 0° C. After cooling again to −20° C., 15 ml of methanol and 133 mg (3.51 mmol) of sodium borohydride were added to the reaction mixture. The reaction mixture was stirred for 2 hours at 0° C. and acidified to pH=2 with diluted hydrochloric acid. After the organic solvent was removed by distillation under vacuum, the residue was extracted with ethyl ether. The organic layer was washed with a saturated aqueous solution of sodium chloride and dried with anhydrous magnesium sulphate. The product was purified using silica gel column chromatography to obtain an alcohol derivative. This compound was dissolved into 26 ml of ethyl ether and the resulting solution was cooled to 0° C. John's reagent, previously prepared from 7.02 g (70.2 mmol) of CrO$_3$, 7.02 ml of H$_2$SO$_4$ and 28.1 ml of H$_2$O, was slowly added thereto, and the mixture was stirred for 15 hours at room temperature. The mixture was extracted with ethyl ether, washed with a saturated aqueous sodium chloride solution and dried using anhydrous magnesium sulphate. The product was purified using silica gel column chromatography to obtain 420 mg of the desired product. The yield was 52.0%. Part of this product was esterified to the methyl ester which was analyzed by gas chromatography with a chiral stationary phase to obtain an optical purity of 85.9%e.e.

$^1$H-NMR(CDCl$_3$)δ: 0.89 (t, 3H, J=7.0 Hz), 1.18–1.70 (m, 8H), 1.95–2.28 (m, 2H), 8.25 (br, 1H).

MS(m/z): 231 (M$^+$), 211, 193.

(2) Synthesis of 5-(4-decylphenyl)-2-(4-((R)-2-fluoro-2-trifluoromethyloctanoyloxy)phenyl)-1,3-pyrimidine The above-titled compound was prepared in the same manner as in Example 1, except for replacing 5-(3-fluoro-4-octyloxyphenyl)-2-(3-fluoro-4-hydroxyphenyl)-1,3-pyrimidine with 5-(4-decylphenyl)-2-(4-hydroxyphenyl)-1, 3-pyrimidine and replacing (S)-2-fluoroheptanoic acid with (R)-2-fluoro-2-trifluoromethyloctanoic acid.

$^1$H-NMR(CDCl$_3$)δ: 0.88 (t, 3H, J=6.9 Hz), 0.91 (t, 3H, J=7.1 Hz), 1.20–1.55 (m, 21H), 1.6–1.75 (m, 3H), 2.10–2.40 (m, 2H), 2.68 (t, 2H, J=7.7 Hz), 7.27 (d, 2H, J=9.0 Hz), 7.34 (d, 2H, J=8.4 Hz), 7.55 (d, 2H, J=8.4 Hz), 8.57 (d, 2H, J=9.0 Hz), 9.00 (s, 2H)

MS(m/z): 600 (M$^+$)

This compound melted at 45.2° C. to exhibit an unidentified high order smectic phase, and changed to an isotropic phase at 70.8° C.

This compound was added in an amount of 10.0% by weight to the compound of Reference Example 1 to obtain a liquid crystal composition. This composition changed from an isotropic phase at 124.6° C. to a SmA phase, became a SmC* phase at 121.1° C., and then exhibited an antiferroelectric liquid crystal phase at 120.9° C. (Tc).

The resulting antiferroelectric liquid crystal composition was injected into a liquid crystal cell, and the measured threshold voltage was 44.4 V at Tc-15° C. The compound of Reference Example 1 had a threshold voltage of 59 V at a temperature of (Tc-15° C.). Thus, it can be seen that incorporation of the compound of Example 15 reduced the threshold voltage of the resulting composition, thus making it possible to obtain a stable antiferroelectric liquid crystal composition having improved properties.

Example 16

Synthesis of 5-(4-decylphenyl)-2-(4-((R)-2-fluoro-2-trifluoromethyldecanoyloxy)phenyl)-1,3-pyrimidine (1) Synthesis of (R)-2-fluoro-2-trifluoromethyldecanoic acid (1-1) Synthesis of 2-fluoro-2-trifluoromethyl-4-decenamide Into a reaction flask were charged 2.0 g (15.6 mmol) of (R)-1-octen-3-ol (96.0%e.e.), 4.4 ml (31.3 mmol) of triethylamine and 40 ml of dichloromethane, and the reaction mixture was cooled to 0° C. Holding the temperature at 0° C., 3.5 ml (15.6 mmol) of hexafluoropropene diethylamine was added dropwise to the mixture. After the addition, the reaction mixture was stirred for 2 hours at 0° C. and 48 hours at room temperature. Into the mixture was added a saturated aqueous solution of sodium bicarbonate, and the mixture was extracted with dichloromethane. The organic layer was dried with anhydrous magnesium sulphate and then concentrated. The raw product was purified using silica gel column chromatography to obtain 3.26 g of the desired compound. The yield was 67.2%.

$^1$H-NMR(CDCl$_3$)δ: 0.89 (t, 3H, J =7.1 Hz), 1.15 (t, 3H, J =7.1 Hz), 1.18 (t, 3H, J=7.1 Hz), 1.21–1.40 (m, 6H), 2.00 (m, 2H), 2.61 (m, 1H), 3.07 (m, 1H), 3.30–3.59 (m, 4H), 5.32 (dt, 1H, J =7.2 Hz, J =15.3 Hz), 5.86 (dt, 1H, J =6.7 Hz, J=15.3 Hz).

MS(m/z): 312 (M$^+$+1), 220, 100.

(1-2) Synthesis of 2-fluoro-2-trifluoromethyldecanamide

Into a solution of 3.0 g (9.65 mmol) of 2-fluoro-2-trifluoromethyl-4-decenamide in 30 ml of methanol, palladium-carbon (75 mg) was added under nitrogen. After the atmosphere was replaced with hydrogen, the mixture was stirred for 24 hours. To remove the catalyst, the resulting mixture was filtered with celite and the filtrate was concentrated. The raw product was purified using silica gel column chromatography to obtain 3.0 g of the desired compound. The yield was 99.3%.

$^1$H-NMR(CDCl$_3$)δ: 0.89 (t, 3H, J=7.0 Hz), 1.17 (t, 3H, J=7.1 Hz), 1.21 (t, 3H, J=7.0 Hz), 1.27–1.54 (m, 12H), 1.90 (m, 1H), 2.35 (m, 1H), 3.30–3.70 (m, 4H).

MS(m/z): 313 (M$^+$), 201, 100.

(1-3) Synthesis of (R)-2-fluoro-2-trifluoromethyloctanoic acid

Into a suspension of lithium aluminium hydride (61 mg, 1.60 mmol) in tetrahydrofuran (7.0 ml) was slowly added a solution of 1.0 g of 2-fluoro-2-trifluoromethyloctanamide (3.19 mmol) in 3.0 ml of tetrahydrofuran at −20° C., and the reaction mixture was stirred for 6 hours at 0° C. After cooling again to −20° C., 15 ml of methanol and 182 mg (3.19 mmol) of sodium borohydride were added to the reaction mixture. The reaction mixture was stirred for 2 hours at 0° C. and acidified to pH =2 with diluted hydrochloric acid. After the organic solvent was removed by distillation under vacuum, the residue was extracted with ethyl ether. The organic layer was washed with a saturated aqueous sodium chloride solution and dried with anhydrous magnesium sulphate. The product was purified using silica gel column chromatography to obtain an alcohol derivative. This compound was dissolved in 26 ml of ethyl ether, and the resulting organic solution was cooled to 0° C. John's reagent, previously prepared from 6.4 g (64 mmol) of CrO$_3$, 6.4 ml of H$_2$SO$_4$ and 26 ml of H$_2$O, was slowly added thereto, and the mixture was stirred for 15 hours at room temperature. The mixture was extracted with ethyl ether, washed with a saturated aqueous solution of sodium chloride and dried with anhydrous magnesium sulphate. The product was purified using silica gel column chromatography to obtain 270 mg of the desired product. The yield was 32.1%. Part of this product was esterified to the methyl ester which was analyzed by gas chromatography with a chiral stationary phase to obtain an optical purity of 86.7%e.e.

$[\alpha]_D^{25}$=+3.0°(c=2.0, CHCl$_3$).

$^1$H-NMR(CDCl$_3$)δ: 0.89 (t, 3H, J=7.1 Hz), 1.15–1.70 (m, 12H), 1.95–2.30 (m, 2H), 9.65 (br, 1H).

MS(m/z): 243 (M$^+$–CH$_3$), 174, 146.

(2) Synthesis of 5-(4-decylphenyl)-2-(4-((R)-2-fluoro-2-trifluoromethyldecanoyloxy)phenyl)-1,3-pyrimidine The synthetic procedure of Example 15 was followed, except for replacing (R)-2-fluoro-2-trifluoromethyloctanoic acid with (R)-2-fluoro-2-trifluoromethyldecanoic acid in step (2).

$^1$H-NMR(CDCl$_3$)δ ppm: 0.88 (t, 3H, J=6.9 Hz), 0.89 (t, 3H, J=7.0 Hz), 1.20–1.55 (m, 25H), 1.60–1.80 (m, 3H), 2.10–2.40 (m, 2H), 2.68 (t, 2H, J=7.8 Hz), 7.27 (d, 2H, J=8.9 Hz), 7.35 (d, 2H, J=8.4 Hz), 7.55 (d, 2H, J=8.4 Hz), 8.57 (d, 2H, J=9.0 Hz), 9.01 (s, 2H)

MS(m/z): 628 (M$^+$)

This compound melted at 46.4° C. to exhibit an unidentified high order smectic phase and changed to an isotropic phase at 66.8° C.

Example 17

Synthesis of 5-(4-decylphenyl)-2-(4-((R)-2-fluoro-2-trifluoromethylhexanoyloxy)phenyl)-1,3-pyrimidine (1) Synthesis of (R)-2-fluoro-2-trifluoromethylhexanoic acid The synthetic procedure of Example 15 was followed, except for replacing (R)-1-hexen-3-ol with (R)-1-buten-3-ol in the step (1-1) to obtain (R)-2-fluoro-2-trifluoromethylhexanoic acid.

$^1$H-NMR(CDCl$_3$)δ: 0.93 (t, 3H, J=7.1 Hz), 1.10–1.70 (m, 4H), 1.95–2.38 (m, 2H), 8.14 (br, 1H).

MS(m/z): 202 (M$^+$), 134, 91.

(2) Synthesis of 5-(4-decylphenyl)-2-(4-((R)-2-fluoro-2-trifluoromethylhexanoyloxy)phenyl)-1,3-pyrimidine The synthetic procedure of Example 15 (2) was followed, except for replacing (R)-2-fluoro-2-trifluoromethyloctanoic acid with (R)-2-fluoro-2-trifluoromethylhexanoic acid to obtain the above-titled compound.

¹H-NMR(CDCl₃)δ ppm 0.88 (t, 3H, J=6.9 Hz), 0.99 (t, 3H, J=7.2 Hz), 1.20–1.40 (m, 14H), 1.42–1.55 (m, 3H), 1.63–1.75 (m, 3H), 2.10–2.42 (m, 2H), 2.68 (t, 2H, J=7.7 Hz), 7.28 (d, 2H, J=9.0 Hz), 7.35 (d, 2H, J=8.3 Hz), 7.55 (d, 2H, J=8.3 Hz), 8.57 (d, 2H, J=8.9 Hz), 9.01 (s, 2H)
MS(m/z): 572 (M⁺)

This compound melted to provide an unidentified high order smectic phase at 56.8° C., changed to another unidentified high order smectic phase at 71.1° C., and exhibited an isotropic phase at 83.6° C.

Example 18

5-(4-decylphenyl)-2-(4-((2S,3R)-2.3-dimethylheptanoyloxy)phenyl)-1,3-pyrimidine

The synthetic procedure of Example 15 (2) was followed, except for replacing (R)-2-fluoro-2-trifluoromethyloctanoic acid with (2S,3R)-2,3-dimethylheptanoic acid to obtain the above-titled compound.

¹H-NMR(CDCl₃)δ ppm: 0.88 (t, 3H, J=7.0 Hz), 0.93 (t, 3H, J=7.0 Hz), 0.99 (d, 3H, J=6.8 Hz), 1.23 (d, 3H, J=7.1 Hz), 1.20–1.50 (m, 20H), 1.60–1.72 (m, 2H), 2.00–2.12 (m, 1H), 2.63–2.72 (m, 3H), 7.21 (d, 2H, J=8.9 Hz), 7.34 (d, 2H, J=8.3 Hz), 7.55 (d, 2H, J=8.3 Hz), 8.52 (d, 2H, J =8.9 Hz), 8.99 (s, 2H)
MS(m/z): 528 (M⁺)

This compound melted at 70.3° C. to provide a SmC* phase, changed to a SmA phase at 111.7° C., and then to an isotropic phase at 113.2° C.

Example 19

Synthesis of 5-(4-decylphenyl)-2-(4-((2S,3S)-2,3-dimethylheptanoyloxy)phenyl)-1,3-pyrimidine The synthetic procedure of Example 15 was followed, except for replacing (R)-2-fluoro-2-trifluoromethyloctanoic acid with (2S,3S)-2,3-dimethylheptanoic acid to obtain the above-titled compound.

¹H-NMR(CDCl₃)δ ppm 0.88 (t, 3H, J=6.9 Hz), 0.93 (t, 3H, J=7.0 Hz), 1.06(d, 3H, J=6.8 Hz), 1.28 (d, 3H, J=7.0 Hz), 1.20–1.47 (m, 22H), 1.60–1.70 (m, 2H), 1.87–1.98 (m, 1H), 2.60–2.72 (m, 3H), 7.22 (d, 2H, J=8.9 Hz), 7.34 (d, 2H, J=8.3 Hz), 7.55 (d, 2H, J=8.3 Hz), 8.52 (d, 2H, J=8.9 Hz), 8.99 (s, 2H)
MS(m/z): 529 (M⁺+1)

This compound melted at 89.8° C. to provide a SmC* phase, changed to a SmA phase at 130° C., and then to an isotropic phase at 135.6° C.

This compound was added in an amount of 30.0% by weight to the compound of Reference Example 1 to obtain a liquid crystal composition. This composition changed from an isotropic phase at 129.5° C. to a SmA phase, and then exhibited an antiferroelectric liquid crystal phase at 122.1° C. (Tc).

The resulting antiferroelectric liquid crystal composition was injected into a liquid crystal cell and the measured threshold voltage was 33.6 V at Tc-15° C. The compound of Reference Example 1 had a threshold voltage of 59 V at a temperature of (Tc-15° C.). Thus, it can be seen that incorporation of the compound of Example 19 reduced the threshold voltage of the resulting composition, thus making it possible to obtain a stable antiferroelectric liquid crystal composition having improved properties.

Example 20

Synthesis of 5-(4-decylphenyl)-2-(4-((1S,2R)-2-methyl-1-cyclohexanecarbonyloxy)phenyl)-1,3-pyrimidine The synthetic procedure of Example 15 was followed, except for replacing (R)-2-fluoro-2-trifluoromethyloctanoic acid with (1S,2R)-2-methyl-1-cyclohexanecarboxylic acid to obtain the above-titled compound.

¹H-NMR(CDCl₃)δ ppm 0.88 (t, 3H, J=6.9 Hz), 1.09 (d, 3H, J=7.0 Hz), 1.18–2.00 (m, 24H), 2.36 (m, 1H), 2.67 (t, 2H, J=7.7 Hz), 2.76–2.85 (m, 1H), 7.22 (d, 2H, J=8.9 Hz), 7.33 (d, 2H, J=8.3 Hz), 7.54 (d, 2H, J=8.3 Hz), 8.51 (d, 2H, J=8.8 Hz), 8.99 (s, 2H)
MS(m/z): 512 (M⁺)

This compound melted at 123.5° C. to provide a SmC* phase, changed to a SmA phase at 149.8° C., and then to an isotropic phase at 152.2° C.

Example 21

Synthesis of 5-(4-decylphenyl)-2-(3-fluoro-4-((1S,2R)-2-methyl-1-cyclohexanecarbonyloxy)phenyl)-1,3-pyrimidine The above-titled compound was synthesized in the same manner as in Example 20, except for replacing 5-(4-decylphenyl)-2-(4-hydroxyphenyl)-1,3-pyrimidine used in Example 20 with 5-(4-decylphenyl)-2-(3-fluoro-4-hydroxyphenyl)-1,3-pyrimidine.

¹H-NMR(CDCl₃)δ ppm: 0.88 (t, 3H, J=6.9 Hz), 1.10 (d, 3H, J=7.1 Hz), 1.18–2.00 (m, 24H), 2.33 (m, 1H), 2.68 (t, 2H, J=7.7 Hz), 2.82–2.90 (m, 1H), 7.08–7.25 (m, 1H), 7.34 (d, 2H, J=8.2 Hz), 7.54 (d, 2H, J=8.3 Hz), 8.28–8.33 (m, 2H), 8.99 (s, 2H)
MS(m/z): 531 (M⁺+1)

This compound melted at 112.3° C. to show an unidentified high order smectic phase, exhibited a SmC* phase at 120.9° C., changed to a SmA phase at 142.3° C., and then to an isotropic phase at 145.8° C.

This compound was added in an amount of 19.9% by weight to the compound of Reference Example 1 to obtain a liquid crystal composition. This composition changed from an isotropic phase at 130.3° C. to a SmA phase, and then exhibited an antiferroelectric liquid crystal phase at 130.1° C. (Tc).

The resulting antiferroelectric liquid crystal composition was injected into a liquid crystal cell, and the measured threshold voltage was 57.6 V at Tc-15° C. The compound of Reference Example 1 had a threshold voltage of 59 V at a temperature of (Tc-15° C.). Thus, it can be seen that the incorporation of the compound of Example 21 reduced the threshold voltage of the resulting composition, thus making it possible to obtain a stable antiferroelectric liquid crystal composition even when the compound of Example 21 was added in an amount of about 20%.

Example 22

Synthesis of 5-(4-decylphenyl)-2-(3-fluoro-4-((1S,2R)-2-butyl-1-cyclohexanecarbonyloxy)phenyl)-1,3-pyrimidine The synthetic procedure of Example 20 was followed, except for replacing (1S,2R)-2-methyl-1-cyclohexanecarboxylic acid with (1S,2R)-2-butyl-1-cyclohexanecarboxylic acid to obtain the above-titled compound.

¹H-NMR(CDCl₃)δ ppm: 0.89 (t, 3H, J=6.9 Hz), 0.93 (t, 3H, J=7.1 Hz), 1.22–1.85 (m, 29H), 1.92–2.04 (m, 2H), 2.68 (t, 2H, J=7.7 Hz), 2.90–2.97 (m, 1H), 7.21–7.25 (m, 1H), 7.42 (d, 2H, J=8.4 Hz), 7.55 (d, 2H, J =8.3 Hz), 8.29–8.34 (m, 2H), 9.00 (s, 2H)
MS(m/z): 573 (M⁺+1)

This compound melted at 95.4° C. to provide an isotropic phase.

Example 23

Synthesis of 5-(4-decylphenyl)-2-(4-((2S,3R)-2-methyl-3-fluorohexanoyloxy)phenyl)-1,3-pyrimidine The above-titled compound was prepared in the same manner as in Example 1, except for replacing 5-(3-fluoro-4-octyloxyphenyl)-2-(3-fluoro-4-hydroxyphenyl)-1,3- pyrimidine with 5-(4-decylphenyl)-2-(4-hydroxyphenyl)-1,3-pyrimidine and replacing (S)-2-fluoroheptanoic acid with (2S,3R)-2-methyl-3-fluorohexanoic acid.

$^1$H-NMR(CDCl$_3$)δ ppm: 0.88 (t, 3H, J=6.9 Hz), 1.01 (t, 3H, J=7.0 Hz), 1.20–1.90 (m, 20H), 1.41 (d, 3H, J=7.1 Hz), 2.68 (t, 2H, J=7.8 Hz), 2.87–2.98 (m, 1H), 4.92 (dm, 1H, J=48.1 Hz), 7.23 (d, 2H, J=9.0 Hz), 7.34 (d, 2H, J=8.3 Hz), 7.55 (d, 2H, J=8.3 Hz), 8.53 (d, 2H, J=9.0 Hz), 9.00 (s, 2H)
MS(m/z): 518 (M$^+$)

This compound melted at 99.6° C. to provide a SmC* phase, changed to a SmA phase at 133.9° C., and then to an isotropic phase at 141.4° C.

This compound was added in an amount of 10.0% by weight to the compound of Reference Example 1 to obtain a liquid crystal composition. This composition changed from an isotropic phase to an antiferroelectric liquid crystal phase at 127.1° C. (Tc).

The resulting antiferroelectric liquid crystal composition was injected into a liquid crystal cell, and the measured threshold voltage was 37.2 V at Tc-15° C. The compound of Reference Example 1 had a threshold voltage of 59 V at a temperature of (Tc-15° C.). Thus, it can be seen that incorporation of the compound of Example 23 reduced the threshold voltage of the resulting composition, thus making it possible to obtain a stable antiferroelectric liquid crystal composition having improved properties.

Example 24
Synthesis of 5-(4-octyloxyphenyl)-2-(4-((R)-1-methylbutyloxymethyl)phenyl)-1,3-pyrimidine The procedure of Example 9 was followed, except for replacing 5-(4-decylphenyl)-2-(4-ethoxycarbonylphenyl)-1,3-pyrimidine in step (1) of Example 9 with 5-(4-octyloxyphenyl)-2-(4-methoxycarbonylphenyl)-1,3-pyrimidine and replacing (R)-1,1,1-trifluoro-2-octanol used in step (3) of Example 9 with (R)-2-pentanol to obtain the above-titled compound.

$^1$H-NMR(CDCl$_3$)δ ppm: 0.90 (t, 3H, J=7.0 Hz), 0.92 (t, 3H, J=7.3 Hz), 1.22 (d, 3H, J=6.1 Hz), 1.25–1.70 (m, 14H), 1.78–1.88 (m, 2H), 3.50–3.60 (m, 1H), 4.02 (t, 2H, J=6.6 Hz), 4.55 (d, 1H, J=12.3 Hz), 4.66 (d, 1H, J=12.3 Hz), 7.04 (d, 2H, J=8.9 Hz), 7.48 (d, 2H, J=8.6 Hz), 7.55 (d, 2H, J=8.8 Hz), 8.44 (d, 2H, J=8.5 Hz), 8.97 (s, 2H)
MS(m/z): 460 (M$^+$)

This compound melted to exhibit an antiferroelectric liquid crystal phase at 52.0° C., changed to a SmC* phase at 115.8° C., and then to an isotropic phase at 149.4° C.

This compound was added in an amount of 19.9% by weight to Reference Example 1 to obtain a liquid crystal composition. This composition changed from an isotropic phase to a SmC* phase at 128.3° C., and exhibited an antiferroelectric liquid crystal phase at 125.5° C. (Tc).

The resulting antiferroelectric liquid crystal composition was injected into a liquid crystal cell, and the measured threshold voltage was 47.6 V at Tc-15° C. The compound of Reference Example 1 had a threshold voltage of 59 V at a temperature of (Tc-15° C.). Thus, it can be seen that incorporation of the compound of Example 24 reduced the threshold voltage of the resulting composition, thus making it possible to obtain a stable antiferroelectric liquid crystal composition having improved properties.

The optically active compound of the present invention has good miscibility with many known antiferroelectric liquid crystal compounds and thus can provide a liquid crystal material having a reduced threshold voltage. Furthermore, a liquid crystal composition containing an optically active compound of the present invention can be incorporated into electro-optic elements employing an antiferroelectric liquid crystal.

While the invention has been described in detail and with reference to specific embodiments thereof, it will be apparent to one skilled in the art that various changes and modifications can be made therein without departing from the spirit and scope thereof.

What is claimed is:

1. An optically active compound, represented by the following general formula (1):

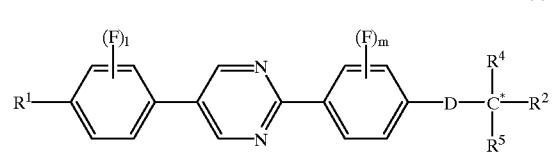

(1)

wherein R$^1$ represents an alkyl or alkoxy group having 5 to 14 carbon atoms; R$^2$ represents an alkyl group having 2 to 12 carbon atoms; 1 and m each represents 0 or 1; D represents —OCO—,—CH$_2$—O— or —OCOC*R$^3$H—, with the proviso that when D is —OCO—, R$^4$ represents a fluorine atom or a trifluoromethyl group and R$^5$ represents a hydrogen atom or a fluorine atom, when D is —CH$_2$—O—, R$^4$ represents a methyl group or a trifluoromethyl group and R$^4$ represents a hydrogen atom, R$^5$ is a hydrogen atom, and R$^2$ may form a ring with R$^3$; and C* represents an asymmetric carbon atom.

2. An antiferroelectric liquid crystal composition containing an antiferroelectric liquid crystal compound and at least one optically active compound represented by the following general formula (1):

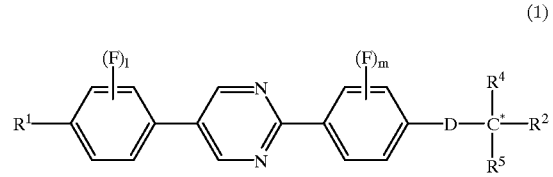

(1)

wherein R$^1$ represents an alkyl or alkoxy group having 5 to 14 carbon atoms; R$^2$ represents an alkyl group having 2 to 12 carbon atoms; 1 and m each represents 0 or 1; D represents —OCO—,—CH$_2$—O— or —OCOC*R$^3$H—, with the proviso that when D is —OCO—, R$^4$ represents a fluorine atom or a trifluoromethyl group and R$^5$ represents a hydrogen atom or a fluorine atom, when D is —CH$_2$—O—, R$^4$ represents a methyl group or a trifluoromethyl group and R$^5$ represents a hydrogen atom, when D is —OCOC*R$^3$H—, R$^3$ is a methyl group, R$^4$ is a fluorine atom or an alkyl group having 1 to 5 carbon atoms, R$^5$ is a hydrogen atom, and R$^2$ may form a ring with R$^3$; and C* represents an asymmetric carbon atom.

3. A process for reducing the threshold voltage of an antiferroelectric liquid crystal composition, which comprises incorporating at least one optically active compound represented by the following general formula (1) into an antiferroelectric liquid crystal or composition thereof to reduce the threshold voltage of the resulting composition:

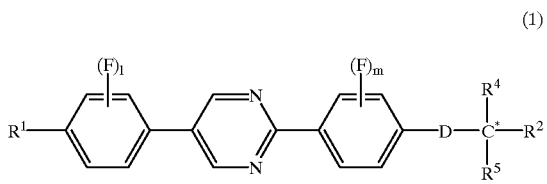

(1)

wherein $R^1$ represents an alkyl or alkoxy group having 5 to 14 carbon atoms; $R^2$ represents an alkyl group having 2 to 12 carbon atoms; 1 and m each represents 0 or 1; D represents —OCO—,—CH$_2$—O— or —OCOC*R$^3$H—, with the proviso that when D is —OCO—, $R^4$ represents a fluorine atom or a trifluoromethyl group and $R^5$ represents a hydrogen atom or a fluorine atom, when D is —CH$_2$—O—, $R^4$ represents a methyl group or a trifluoromethyl group and $R^5$ represents a hydrogen atom, when D is —OCOC*R$^3$H—, $R^3$ is a methyl group, $R^4$ is a fluorine atom or an alkyl group having 1 to 5 carbon atoms, $R^5$ is a hydrogen atom, and $R^2$ may form a ring with $R^3$; and C* represents an asymmetric carbon atom.

4. A process for producing of an optically active compound represented by the following general formula (1):

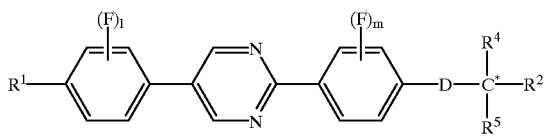

(1)

wherein $R^1$ represents an alkyl or alkoxy group having 5 to 14 carbon atoms; $R_2$ represents an alkyl group having 2 to 12 carbon atoms; 1 and m each represents 0 or 1; D represents —OCO—,—CH$_2$—O— or —OCOC*R$^3$H—, with the proviso that when D is —OCO—, $R^4$ represents a fluorine atom or a trifluoromethyl group and $R^5$ represents a hydrogen atom or a fluorine atom, when D is —CH$_2$—O—, $R^4$ represents a methyl group or a trifluoromethyl group and $R^5$ represents a hydrogen atom, when D is —OCOC*R$^3$H—, $R^3$ is a methyl group, $R^4$ is a fluorine atom or an alkyl group having 1 to 5 carbon atoms, $R^5$ is a hydrogen atom, and $R^2$ may form a ring with $R^3$; and C* represents an asymmetric carbon atom, which comprises reacting a compound represented by the following general formula (2):

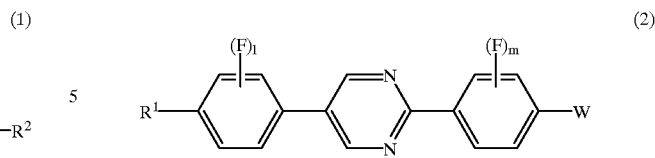

(2)

wherein $R^1$ represents an alkyl or alkoxy group having 5 to 14 carbon atoms; 1 and m each represents 0 or 1; and W represents hydroxy group, chloromethyl group or bromomethyl group,
with the following compound represented by general formula (3):

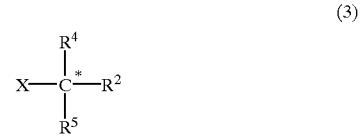

(3)

wherein $R^2$ represents an alkyl group having 2 to 12 carbon atoms; X represents COOH, COCl, a hydroxymethyl group, —C*R$^3$HCOOH or —C*R$^3$HCOCl with the proviso that when X is COOH or COCl, $R^4$ represents a fluorine atom or a trifluoromethyl group and $R^5$ represents a hydrogen atom or a fluorine atom, when X is a hydroxymethyl group, $R^4$ represents a methyl group or a trifluoromethyl group and $R^5$ represents a hydrogen atom, when X is —C*R$^3$HCOOH or —C*R$^3$HCOCl, $R^3$ is a methyl group, $R^4$ is a fluorine atom or an alkyl group of 1 to 5 carbon atoms, $R^5$ is a hydrogen atom, and $R^2$ may form a ring with $R^3$; and C* represents an asymmetric carbon atom.

5. A process for producing an optically active carboxylic acid represented by the following general formula (4):

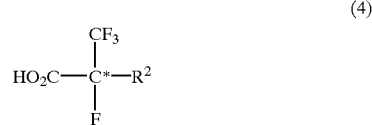

(4)

wherein $R^2$ represents an alkyl group having 4 to 12 carbon atoms; and C* represents an asymmetric carbon atom, which comprises reacting an optically active 1-alkylallylalcohol with hexafluoropropene diethylamine.

* * * * *